United States Patent

(12) United States Patent
Farrar et al.

(10) Patent No.: US 8,221,588 B2
(45) Date of Patent: Jul. 17, 2012

(54) STORAGE STABLE SOLUTIONS OF OPTICAL BRIGHTENERS

(75) Inventors: John Martin Farrar, Leeds (GB); Andrew Clive Jackson, Harrogate (GB); Margaret Mahon, Bradford (GB)

(73) Assignee: Clariant Finance (BVI) Limited, Tortola (VG)

( * ) Notice: Subject to any disclaimer, the term of this patent is extended or adjusted under 35 U.S.C. 154(b) by 736 days.

(21) Appl. No.: 11/989,993

(22) PCT Filed: Jul. 12, 2006

(86) PCT No.: PCT/EP2006/064152
§ 371 (c)(1),
(2), (4) Date: Feb. 1, 2008

(87) PCT Pub. No.: WO2007/017336
PCT Pub. Date: Feb. 15, 2007

(65) Prior Publication Data
US 2010/0159763 A1    Jun. 24, 2010

(30) Foreign Application Priority Data
Aug. 4, 2005   (EP) .................... 05016952

(51) Int. Cl.
*D21H 17/07*   (2006.01)
*D21H 21/30*   (2006.01)
*C07D 251/12*  (2006.01)
*D06L 3/12*    (2006.01)

(52) U.S. Cl. .......... 162/162; 162/72; 162/158; 162/184; 162/185; 8/648; 427/158; 442/130; 544/193.2

(58) Field of Classification Search ........ 162/72, 162/158, 16, 2, 184, 185; 8/648; 427/158; 442/130; 544/193.2
See application file for complete search history.

(56) References Cited

U.S. PATENT DOCUMENTS

| 3,957,710 | A | * | 5/1976 | Rohmann et al. ............. 524/475 |
| 4,462,925 | A | | 7/1984 | Littlewood |
| 4,717,502 | A | * | 1/1988 | Schmid .................... 252/301.23 |
| 5,904,739 | A | | 5/1999 | Martini et al. |
| 2004/0074021 | A1 | * | 4/2004 | Farrar et al. ...................... 8/648 |
| 2004/0154764 | A1 | * | 8/2004 | Blum et al. .................. 162/135 |
| 2010/0294447 | A1 | | 11/2010 | Farrar et al. |

FOREIGN PATENT DOCUMENTS

| EP | 376893 | | 12/1989 |
| EP | 884312 | | 12/1998 |
| GB | 1243276 | | 8/1971 |
| GB | 1247765 | | 9/1971 |
| WO | WO 02/055646 | | 7/2002 |
| WO | WO 2004/005617 | A1 * | 1/2004 |
| WO | WO 2005/028749 | | 3/2005 |

OTHER PUBLICATIONS

PCT International Search Report for PCT/EP2006/064152,Oct. 26, 2006.
PCT Written Opinion of the International Searching Authority for PCT/EP 2006/064152, Oct. 26, 2006.
English Abstract for JP 62273266, 11/267/1987.

* cited by examiner

*Primary Examiner* — Matthew Daniels
*Assistant Examiner* — Dennis Cordray
(74) *Attorney, Agent, or Firm* — Anthony A. Bisulca

(57) ABSTRACT

The instant invention relates to storage stable solutions of optical brighteners based on certain salt forms of anilino-substituted bistriazinyl derivatives of 4,4'-diaminostilbene-2,2'-disulphonic acid which do not need extra solubilising additives.

15 Claims, No Drawings

STORAGE STABLE SOLUTIONS OF OPTICAL BRIGHTENERS

This application is a 371 of PCT/EP2006/064152, filed Jul. 12, 2006 and claims priority to European Application No. 05016952.3, filed Aug. 4, 2005.

The instant invention relates to storage stable solutions of optical brighteners based on derivatives of diaminostilbene which do not need extra solubilising additives.

It is well known that the whiteness and thereby the attractiveness of paper, board, textile and non-woven products can be improved by the addition of optical brightening agents (OBAs). The most important optical brighteners in the paper and board industry are anilino-substituted bistriazinyl derivatives of 4,4'-diaminostilbene-2,2'-disulphonic acid. The anilino-substituent may contain additional sulphonic acid groups, which provide a greater water-solubility. Optical brighteners in which the anilino-substituent contain no sulphonic acid groups have a particularly high affinity for cellulose fibres and are especially suitable for use at the wet-end of the paper making process. For ease of handling and metering, the paper and board industry demands that optical brighteners be supplied in a liquid form, preferably in the form of a concentrated aqueous solution. Furthermore, the liquid form has to be stable to prolonged storage over a wide temperature range, typically 4 to 50° C. In the past, solubilising auxiliaries such as urea or ethylene glycol have been added in amounts of up to 30% by weight in order to provide storage stability. These solubilising agents have no affinity for cellulose, however, and contaminate the effluent from the paper mill. There is therefore a demand for anilino-substituted bistriazinyl derivatives of 4,4'-diaminostilbene-2,2'-disulphonic acid which can form stable, concentrated aqueous solutions without the addition of solubilising auxiliaries.

GB 1,243,276 claims bistriazinyl derivatives of 4,4'-diaminostilbene-2,2'-disulphonic acid which contain at least one, preferably two, propionic amide radical(s), as well as their use as optical brightening agents for paper. Disclosed is the preparation and application of a compound of formula (A).

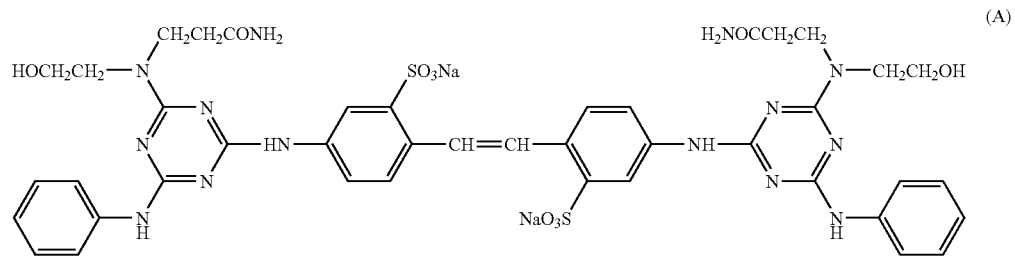

The compound is isolated as a solid, and dissolved in water at a concentration of 0.1% prior to application to an aqueous suspension of cellulose fibres.

Compound (A) is also described in GB 1,247,765.

Compound (A) is also the preferred component of a liquid laundry detergent composition according to EP 376,893 A2. The inventors state that: "The optical brighteners according to the invention are used in powder form or as solutions in water. Such solutions have a content of 18 to 75% by weight of active substance and preferably also contain hydrotropic substances."

There is no suggestion made in GB 1,243,276, GB 1,247,765 or EP 376,893 A2 of any advantage in the use of a counter-ion other than sodium.

WO 02/055646 attempts to solve the problem of forming a stable, concentrated aqueous solution of a disulphonated optical brightener by providing a mixture of two or more bis(triazinylamino) stilbene derivatives. Example 1 describes the preparation of a stable aqueous solution containing 0.2844 mol/kg optical brightener in the form of an equimolar mixture of compounds (B) and (C), each in the form of a mixed sodium/triethanolammonium salt.

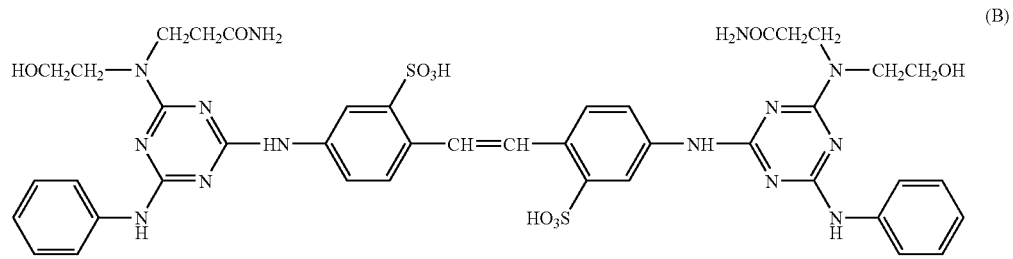

(B)

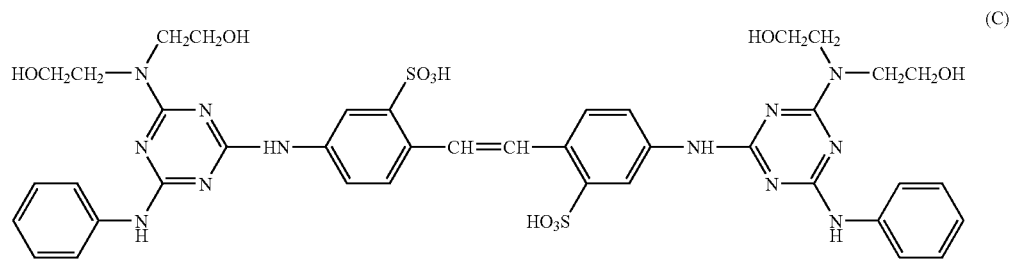

(C)

The storage stability also relies however on the presence of an additive—referred to in WO 02/055646 on page 10 as ($F_1$)—which is employed preferably at a concentration of 0.2 to 3% by weight of solution. Preferred additives ($F_1$) are tertiary alkanolamines, triisopropanolamine being especially preferred.

WO 2005/028749 A1 discloses optical brightener compositions comprising an alkanolamine and a bis(triazinylamino) stilbene derivative. Preferred alkanolamines are 2-amino-2-methyl-1-propanol, 1-amino-2-propanol or a mixture of 2-amino-2-methyl-1-propanol and 2-(N-methylamino)-2-methyl-1-propanol.

Japanese Kokai 62-273266 claims optical brightener compositions comprising quaternary ammonium salts of anionic bis(triazinylamino) stilbene derivatives. The preferred quaternary ammonium ion is a trimethyl-β-hydroxyethylammonium ion.

EP-A-884 312 discloses hydrates of a bis(triazinylamino) stilbene derivative of formula (D)

in which M and $M_1$ independently represent hydrogen, an alkaline-earth metal or ammonium. The hydrates are claimed to enable stable liquid suspensions to be produced with low amounts of formulation auxiliaries.

Papermakers however prefer to use optical brighteners in solution form, e.g. for ease of handling and metering. There is therefore still a need to provide stable, concentrated aqueous solutions of disulphonated optical brighteners, which are free from solubilising auxiliaries.

It has now surprisingly been found that a specific salt form of anilino-substituted bistriazinyl derivatives of 4,4'-diaminostilbene-2,2'-disulphonic acid enable stable concentrated solutions to be formed, without the addition of solubilising auxiliaries.

The present invention therefore provides a compound of formula (1)

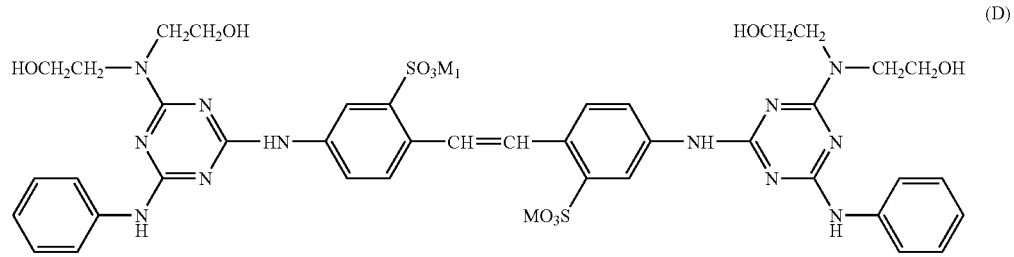

(D)

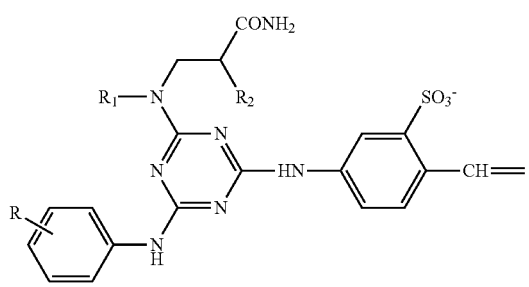

(1)

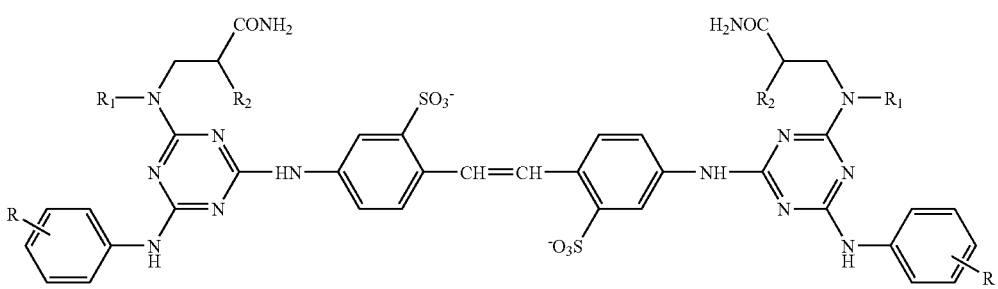

(2)

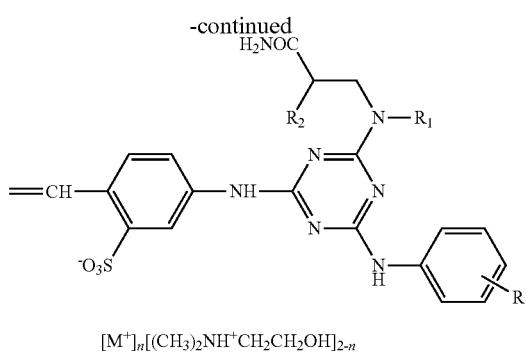

$[M^+]_n[(CH_3)_2NH^+CH_2CH_2OH]_{2-n}$ in which
R is hydrogen or a methyl radical,
$R_1$ is hydrogen, an alkyl radical with 1 to 4 carbon atoms, a β-hydroxyalkyl radical containing 2 to 4 carbon atoms, a 13-alkoxyalkyl radical containing 3 or 4 carbon atoms or $CH_2CH_2CONH_2$,
$R_2$ is hydrogen or a methyl radical,
$M^+$ is $Li^+$, $Na^+$, or $K^+$, and
n is less than or equal to 1.5.

Preferred are compounds in which
R is hydrogen or a methyl radical,
$R_1$ is hydrogen, a methyl radical, a β-hydroxyalkyl radical containing 2 or 3 carbon atoms,
$R_2$ is hydrogen or a methyl radical,
$M^+$ is $Na^+$, and
n is less than or equal to 1.5.

More preferred are compounds in which
R is hydrogen,
$R_1$ is hydrogen, a methyl radical or a β-hydroxyalkyl radical containing 2 carbon atoms,
$R_2$ is hydrogen,
$M^+$ is $Na^+$, and
n is less than or equal to 1.5.

Especially preferred are compounds in which
R is hydrogen,
$R_1$ is $-CH_2CH_2OH$,
$R_2$ is hydrogen,
$M^+$ is $Na^+$, and
n is less than or equal to 1.2.

The present invention also provides a process for the production of the above compounds, the process being characterised in that a compound of formula (2)

in the form of an aqueous solution is converted to a mixed salt form (1) in which at least 25% of the $M^+$ ions associated with the sulphonate groups have been replaced by $(CH_3)_2NH^+CH_2CH_2OH$ ions, either by treatment with 2-dimethylaminoethanol and a mineral acid (for example HCl or $H_2SO_4$) or by sequential treatment with a cationic ion-exchange resin and 2-dimethylaminoethanol. The compound of formula (1) is then optionally isolated, and may be further separated from excess salts and alkanolamine by membrane filtration.

The preferred membrane filtration process is that of ultrafiltration using, e.g, polysulphone, polyvinylidenefluoride, cellulose acetate or thin-film membranes.

The invention further provides an aqueous solution of one or more compounds of formula (1) which may optionally contain one or more carriers, antifreezes, defoamers, solubilizing aids, preservatives, complexing agents etc., as well as organic by-products formed during the preparation of the optical brightener.

Carriers are known to give improved whitening characteristics to pigmented coating brightener compositions and may be, e.g., polyethylene glycols, polyvinyl alcohols or carboxymethylcelluloses.

Antifreezes may be, e.g., urea, diethylene glycol or triethylene glycol.

Solubilizing aids may be, e.g., urea, triethanolamine, triisopropanolamine or 2-dimethylaminoethanol.

Compounds of formula (1) and their solutions are suitable for use as optical brighteners for the whitening of textiles, paper, board and non-wovens. They are particularly useful for the whitening of paper and board, and are suitable for application either to an aqueous suspension of pulp, or to the surface of paper, especially in a pigmented coating composition. They are characterized by high storage stability, yield and ease of application. They are also highly compatible with other additives conventionally employed in the production of cellulosic articles, especially paper and board.

EXAMPLES

The following examples shall demonstrate the instant invention in more details. If not indicated otherwise, "parts" means "parts by weight" and "%" means "% by weight". Membrane filtration was carried out using a G-series thin-film ultrafiltration membrane element supplied by GE Infrastructure Water & Process Technologies.

According to one aspect, the invention is directed to a process for whitening of paper including the steps of providing a pulp suspension, adding 0.01 to 2% by weight based on dry fibre of an aqueous solution according to the invention, producing a paper sheet from said pulp suspension, and pressing and drying the sheet. According to another aspect, the invention is directed to a process for whitening of paper including the steps of preparing an aqueous coating composition by mixing together chalk or other white pigments, one or more dispersing agents, and a primary latex binder adding 0.01 to 3% by weight based on dry pigment of the aqueous solution according to the invention, applying the coating composition to a paper sheet, drying the coated paper sheet.

Example 1

291 parts of an amine of formula (3)

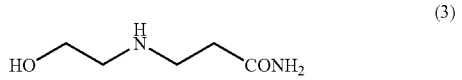

are added at 60° C. to a stirred suspension of 824 parts of a compound of formula (4)

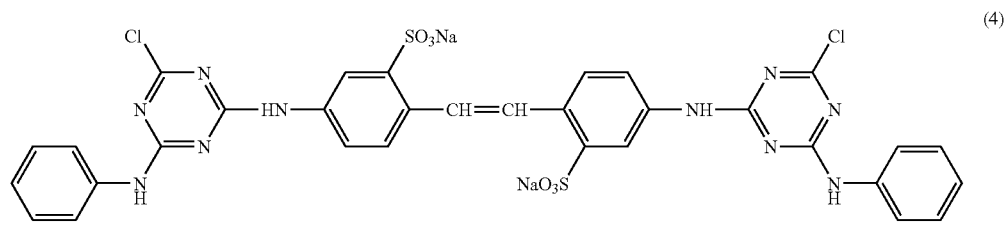

in 7750 parts water. The mixture is heated to reflux and maintained there for 4 hours while controlling the pH to 8.5-9.0 by the addition of sodium hydroxide in the form of a 30% aqueous solution. 44 parts of sodium chloride are added, and the mixture is stirred at reflux for a further 10 minutes. The mixture is then cooled to 90° C. before stirring is stopped. After standing for 10 minutes, the lower phase of oil (1990 parts) containing a compound of formula (A) is separated from the salt-containing aqueous phase and added at 80° C. with stirring to 1570 parts cold water. The solution so-formed is then treated at 50° C. with a solution of 197 parts 2-dimethylaminoethanol in 350 parts cold water and 197 parts 37% aqueous hydrochloric acid. The mixture is stirred at 50° C. for 10 minutes, then cooled to 20° C. After standing for 1 hour, the lower phase of oil is separated, and diluted with water to 5000 parts. Excess sodium chloride and alkanolamine are removed by membrane filtration of the aqueous solution, before removing water by distillation to give 3520 parts of an aqueous solution containing 28% of a compound of formula (5).

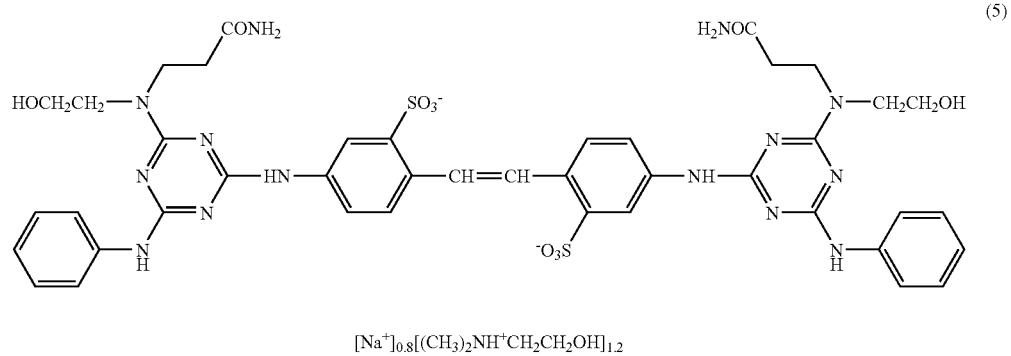

The aqueous solution so-formed is stable to storage at 4° C. for at least two weeks either in the absence or presence of crystal seeds.

Example 2

Comparative Example to Show Advantage Over the $(CH_3)_3N^+CH_2CH_2OH$ Counter-Ion (Claimed in Japanese Kokai 62-273266)

Example 1 is followed up to the point where the oil (1990 parts) is first separated from the salt-containing aqueous phase. The oil is then poured into a stirred solution of 309 parts choline chloride in 2700 parts water. Excess salt is removed by membrane filtration of the aqueous solution, before removing water by distillation to give 3520 parts of an aqueous solution containing 28% of a compound of formula (6).

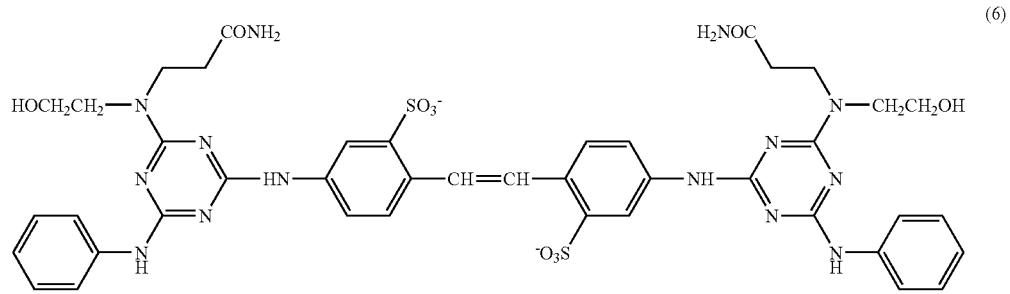

(6)

$[Na^+]_{0.8}[(CH_3)_2N^+CH_2CH_2OH]_{1.2}$

The aqueous solution so-formed precipitates within 4 days on storage at 4° C. in the presence of crystal seeds.

Example 3

Comparative Example to Show Advantage Over the $(CH_3)_2C(NH_3^+)CH_2OH$ Counter-Ion (Claimed in WO 2005/028749 A1)

Example 1 is followed up to the point where the oil from the first phase separation (1990 parts) is diluted with water (1570 parts). The solution so-formed is then treated at 50° C. with a solution of 196 parts 2-amino-2-methyl-1-propanol in 350 parts cold water and 197 parts 37% aqueous hydrochloric acid. The mixture is stirred at 50° C. for 10 minutes, then cooled to 20° C. After standing for 1 hour, the lower phase of oil is separated, and diluted with water to 5000 parts. Excess sodium chloride and alkanolamine are removed by membrane filtration of the aqueous solution, before removing water by distillation to give 3520 parts of an aqueous solution containing 28% of a compound of formula (7).

The aqueous solution so-formed precipitates within 4 days on storage at 4° C. in the presence of crystal seeds.

Example 4

Comparative Example to Show Advantage Over the $H_3N^+CH_2CH_2OH$ Counter-Ion

Example 1 is followed up to the point where the oil from the first phase separation (1990 parts) is diluted with water (1570 parts). The solution so-formed is then treated at 50° C. with a solution of 135 parts ethanolamine in 350 parts cold water and 197 parts 37% aqueous hydrochloric acid. The mixture is stirred at 50° C. for 10 minutes, then cooled to 20° C. After standing for 1 hour, the lower phase of oil is separated, and diluted with water to 5000 parts. Excess sodium chloride and alkanolamine are removed by membrane filtration of the aqueous solution, before removing water by distillation to give 3520 parts of an aqueous solution containing 27% of a compound of formula (8).

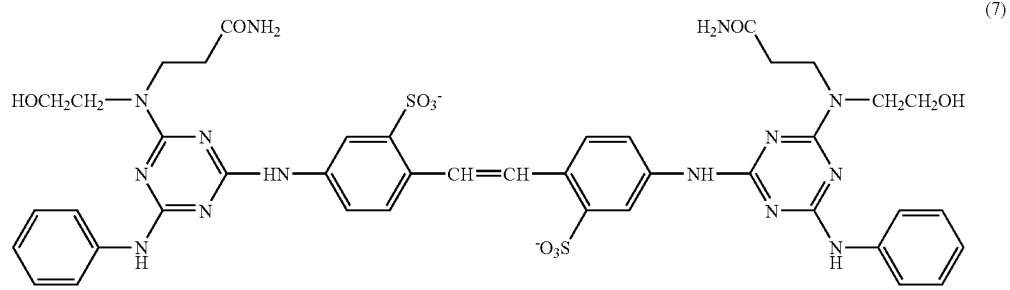

(7)

$[Na^+]_{0.8}[(CH_3)_2C(NH_3^+)CH_2OH]_{1.2}$

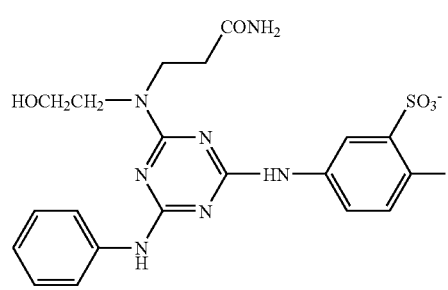
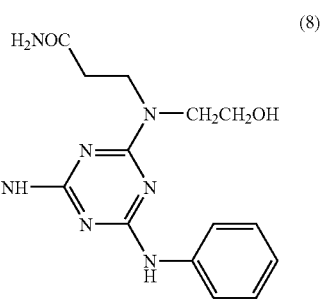

(8)

[Na$^+$]$_{0.8}$[H$_3^+$NCH$_2$CH$_2$OH]$_{1.2}$

The aqueous solution so-formed precipitates within 1 day on storage at 4° C. in the presence of crystal seeds.

Example 5

Comparative Example to Show Advantage Over the Na$^+$Counter-Ion

Example 1 is followed up to the point where the oil from the first phase separation (1990 parts) is diluted with water (1570 parts). Excess sodium chloride is removed by membrane filtration of the aqueous solution at 50° C., before removing water by distillation to give 3520 parts of an aqueous solution containing 26% of a compound of formula (A).

The aqueous solution so-formed precipitates on cooling to room temperature.

Example 6

Example 1 is followed up to the point where the oil (1990 parts) is first separated from the salt-containing aqueous phase. The oil is added at 80° C. with stirring to a solution of 171 parts 37% aqueous hydrochloric acid and 150 parts 2-dimethylaminoethanol in 1582 parts cold water. The mixture is stirred for 10 minutes and cooled to 20° C. After standing for 1 hour, the lower phase of oil is separated, and diluted with water to 5000 parts. The aqueous solution is treated by membrane filtration to remove excess sodium chloride, then concentrated by distillation. A further 7 parts 2-dimethylaminoethanol are added as a solubilizing aid. The strength is adjusted to give 3520 parts of an aqueous solution containing 28% of a compound of formula (9) and 0.2% 2-dimethylaminoethanol.

The aqueous solution so-formed is stable to storage at 4° C. for at least two weeks either in the absence or presence of crystal seeds.

Application Example 1

The product from Preparative Example 1 is added at a range of concentrations from 0.2 to 2% by weight dry fibre to 200 parts of a 2.5% aqueous suspension of a 50:50 mixture of bleached spruce sulphite cellulose and bleached beech sulphite cellulose beaten to a Schopper Riegler wetness of 20° SR. The suspension is stirred for 5 minutes, then diluted to 1000 parts. A paper sheet is then made by drawing the suspension through a wire mesh. After being pressed and dried, the paper is measured for whiteness on a Minolta CM-700d spectrophotometer.

TABLE 1

| Conc. (%) | CIE Whiteness |
|---|---|
| 0 | 77.9 |
| 0.2 | 118.7 |
| 0.4 | 133.6 |
| 0.8 | 142.3 |
| 1.2 | 146.8 |
| 1.6 | 148.2 |
| 2.0 | 148.9 |

The results in the Table clearly demonstrate the excellent whitening effect afforded by a compound of the invention.

Application Example 2

A coating composition is prepared containing 500 parts chalk (commercially available under the trade name Hydro-

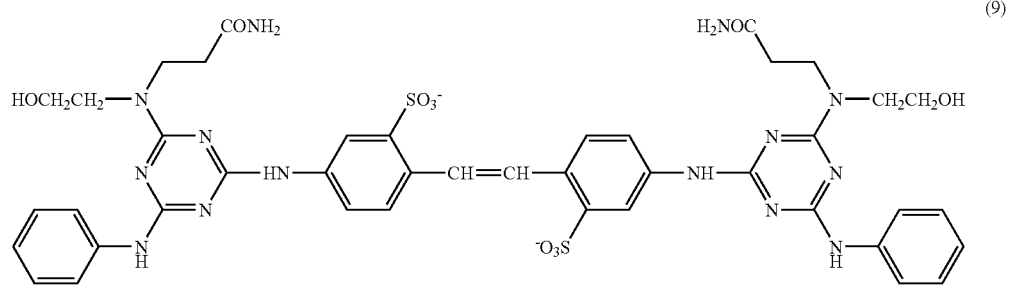

(9)

[Na$^+$]$_{1.1}$[(CH$_3$)$_2$NH$^+$CH$_2$CH$_2$OH]$_{0.9}$ carb 90 from OMYA), 500 parts clay (commercially available under the trade name Kaolin SPS from IMERYS), 470 parts water, 6 parts dispersing agent (a sodium salt of a polyacrylic acid commercially available under the trade name Polysalz S from BASF), 200 parts latex (an acrylic ester copolymer commercially available under the trade name Acronal S320D from BASF), 40 parts of a 10% solution of polyvinyl alcohol (commercially available under the trade name Mowiol 4-98 from Kuraray) in water, and 50 parts of a 10% solution of carboxymethyl cellulose (commercially available under the trade name Finnfix 5.0 from Noviant) in water. The solids content is adjusted to 60% by the addition of water, and the pH is adjusted to 8-9 with sodium hydroxide.

The product from Preparative Example 1 is added at 0.5, 1.0 and 1.5% concentration to the stirred coating composition. The brightened coating composition is then applied to a commercial 75 gsm neutral-sized white paper base sheet using an automatic wire-wound bar applicator with a standard speed setting and a standard load on the bar. The coated paper is then dried for 5 minutes in a hot air flow. The dried paper is allowed to condition, then measured for CIE Whiteness on a calibrated Elrepho spectrophotometer.

TABLE 2

| Conc. (%) | CIE Whiteness |
|---|---|
| 0 | 90.2 |
| 0.5 | 105.2 |
| 1.0 | 108.9 |
| 1.5 | 109.6 |

The results in the Table clearly demonstrate the excellent whitening effect afforded by a compound of the invention.

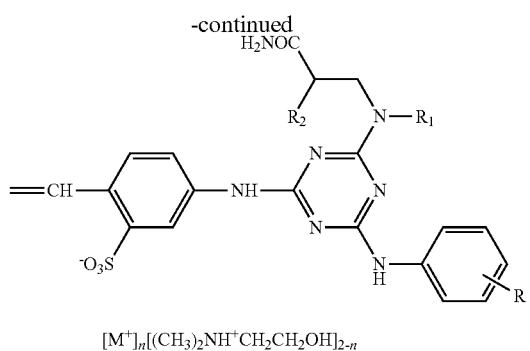

$[M^+]_n[(CH_3)_2NH^+CH_2CH_2OH]_{2-n}$ in which
R is hydrogen,
$R_1$ is —$CH_2CH_2OH$,
$R_2$ is hydrogen,
$M^+$ is $Na^+$, and
n is less than or equal to 1.2.

2. An aqueous solution containing from 20 to 40% by weight of at least one compound of formula (1) according to claim 1.

3. An aqueous solution containing from 25 to 35% by weight of at least one compound of formula (1) according to claim 1.

4. An aqueous solution according to claim 2 containing at least one additional component selected from the group consisting of: carriers, antifreezes, defoamers, solubilizing aids, preservatives, complexing agents, and any organic by-products formed during the preparation of the aqueous solution.

5. A process for preparing a compound of formula (1) according to claim 1 comprising the steps of converting a compound of formula (2)

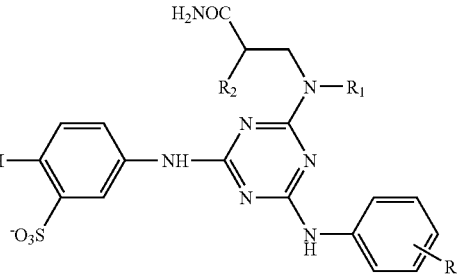

(2)

$[M^+]_2$

The invention claimed is:

1. A compound of formula (1)

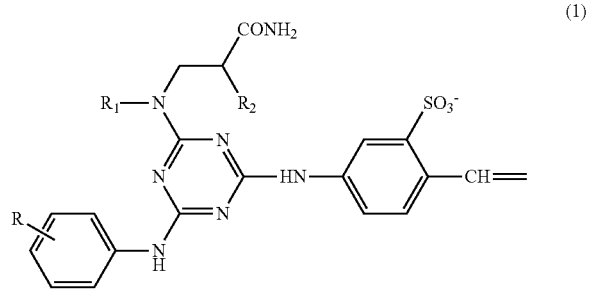

(1)

in the form of an aqueous solution to a mixed salt of formula (1) in which at least 25% of the $M^+$ ions associated with the sulphonate groups have been replaced by $(CH_3)_2NH^+CH_2CH_2OH$ ions, either by treatment with 2-dimethylaminoethanol and a mineral acid or by sequential treatment with a cationic ion-exchange resin and 2-dimethylaminoethanol.

6. A process according to claim 5 wherein the compound of formula (1) is isolated and further separated from excess salts and alkanolamine by membrane filtration.

7. A process for preparing an aqueous solution according to claim 4 wherein the additional components selected from the group consisting of: carriers, antifreezes, defoamers, solubilizing aids, preservatives and complexing agents are added to the aqueous solution.

8. A process for optical brightening of a textile, paper, board or non-woven comprising the step of contacting the textile, paper, board or non-woven with at least one compound according to claim 1.

9. A process for optical brightening of an aqueous suspension of pulp comprising the step of adding at least one compound according to claim 1 to the aqueous suspension of pulp.

10. A process for whitening of paper comprising the steps of providing a pulp suspension, adding 0.01 to 2% by weight based on dry fibre of an aqueous solution according to claim 2, producing a paper sheet from said pulp suspension, pressing and drying the sheet.

11. A process for whitening of paper comprising the steps of preparing an aqueous coating composition by mixing together chalk or other white pigments, one or more dispersing agents, and a primary latex binder adding 0.01 to 3% by weight based on dry pigment of an aqueous solution according to claim 2, applying the coating composition to a paper sheet, drying the coated paper sheet.

12. A textile, paper, board or non-woven made by a process according to claim 8.

13. A paper whitened by a process according to claim 10.

14. A paper whitened by a process according to claim 11.

15. A paper produced by draining an optically brightened aqueous suspension of pulp according to claim 9.

* * * * *